(12) United States Patent
Månsson et al.

(10) Patent No.: US 6,706,499 B2
(45) Date of Patent: Mar. 16, 2004

(54) DNA-EMBEDDING MEDIUM AND METHOD OF USE

(75) Inventors: Per Månsson, Sollentuna (SE); Tomas Lundin, Enkoping (SE)

(73) Assignee: Ascendia AB (SE)

( * ) Notice: Subject to any disclaimer, the term of this patent is extended or adjusted under 35 U.S.C. 154(b) by 72 days.

(21) Appl. No.: 10/011,119

(22) Filed: Nov. 13, 2001

(65) Prior Publication Data

US 2002/0150928 A1 Oct. 17, 2002

Related U.S. Application Data

(62) Division of application No. 09/605,611, filed on Jun. 28, 2000, now abandoned.

(51) Int. Cl.$^7$ .............................. C12P 19/34; C12Q 1/68; C07H 21/04
(52) U.S. Cl. .............................. 435/91.1; 435/4; 435/6; 435/91.2; 435/91.51; 536/23.1; 536/23.5
(58) Field of Search .......................... 435/6, 91.1, 91.2, 435/91.51, 4; 536/23.1, 23.5

(56) References Cited

U.S. PATENT DOCUMENTS 5,612,218 A    3/1997   Busch et al. ............. 435/288.1

FOREIGN PATENT DOCUMENTS

| JP | 63-216476 | | 9/1988 |
|---|---|---|---|
| JP | 7-255469 | * | 10/1995 |
| WO | WO 98/41617 | * | 9/1998 |

OTHER PUBLICATIONS

Nurnberg et al. (Biotechniques (1995) 18(3): 408–9, 411).*
S.D. Finkelstein et al., "Cold–Temperature Plastic Resin Embedding of Liver for DNA– and RNA–Based Genotyping," Journal of Molecular Diagnostics 1(1):17–22 (Nov. 1999).
O.–W. Merten et al., "A Simple Serum–Free Freezing Medium for Serum–Free Cultured Cells," Biologicals 23:185–189 (1995).
G.R. Turbett et al., "The Use of Optimal Cutting Temperature Compound Can Inhibit Amplification by Polymerase Chain Reaction," Diagnostic Molecular Pathology 6(5):298–303 (1997).

* cited by examiner

*Primary Examiner*—Carla J. Myers
*Assistant Examiner*—Alexander H. Spiegler
(74) *Attorney, Agent, or Firm*—Ostrolenk, Faber, Gerb & Soffen, LLP

(57) ABSTRACT

A medium is disclosed for embedding and preserving single cells or a cell tissue for an extended period of time at a temperature not exceeding 0° C. in a state suitable for DNA and/or RNA amplification, comprising an aqueous solution of at least one water-soluble cellulose derivative and, optionally, an osmotic pressure stabilizing agent. A method for preserving single cells or a cell tissue for an extended period of time at a temperature not exceeding 0° C. in a state suitable for DNA and/or RNA amplification using the above medium is also disclosed.

12 Claims, 7 Drawing Sheets

DNA-EMBEDDING MEDIUM AND METHOD OF USE

RELATED APPLICATIONS

This application is a divisional of U.S. patent application Ser. No. 09/605,611, filed Jun. 28, 2000 now abandoned.

FIELD OF THE INVENTION

The present invention relates to a medium for embedding cells and tissues containing native DNA and/or native RNA to preserve its structure when stored. The present invention also relates to a method of using the embedding medium for protecting native DNA/RNA destined for use in DNA/RNA amplification, in particular by PCR and RT-PCR.

BACKGROUND OF THE INVENTION

High copy numbers of specific nucleic acid sequences (fragments) may be obtained from DNA by amplification using the polymerase chain reaction (PCR) or from RNA using the reverse transcriptase polymerase chain reaction (RT-PCR). For details about the PCR, see PCR, *A Practical Approach*, McPherson, Quirke, and Taylor, Eds. IRL Press, Oxford 1991.

Quantitative PCR and RT-PCR are used in assaying pathological conditions of cells and tissues, such as the presence of pathogenic microorganisms and genetic mutations causing malignancy, for instance malignancy in lymphocytes isolated from patients suspected to suffer from lymphoma, for instance, T- or B-cell lymphoma or Hodgkin's disease. Most often cells and tissue sampled for this reason cannot be assayed on the spot but need to be stored for a certain period of time prior to being assayed. It is important that the DNA be preserved in its native state during such storage. The problem of storage is not a minor one since it has been reported (G R. Turbett and Loryn N. Sellner, Diagn. Mol. Pathol. 6(5):298–303, 1997) that preservation of frozen tissue in a widely used embedding medium, Optimal Cutting Temperature™ (OCT) may inhibit PCR and RT-PCR. 'Native DNA' and 'Native RNA' designate native DNA/RNA in a tissue sample as well as isolated native chromosomal DNA/RNA, and sequences thereof.

SUMMARY OF THE INVENTION

It is an object of the invention to provide a medium of the aforementioned kind preserving DNA/RNA in its native state for extended periods of time.

It is another object of the invention to provide a method of using a medium in the preservation of native DNA/RNA in cells and tissues destined for use in DNA/RNA amplification methods.

Further objects of the invention will become apparent from the study of the following summary of the invention, the description of preferred embodiments thereof, and of the appended claims.

BRIEF DESCRIPTION OF THE DRAWINGS

The following drawings comprise a number of electrophoretic separation diagrams on agarose of DNA and RNA obtained in PCR and RT-PCR assays.

DETAILED DESCRIPTION OF THE INVENTION

Figure 1:
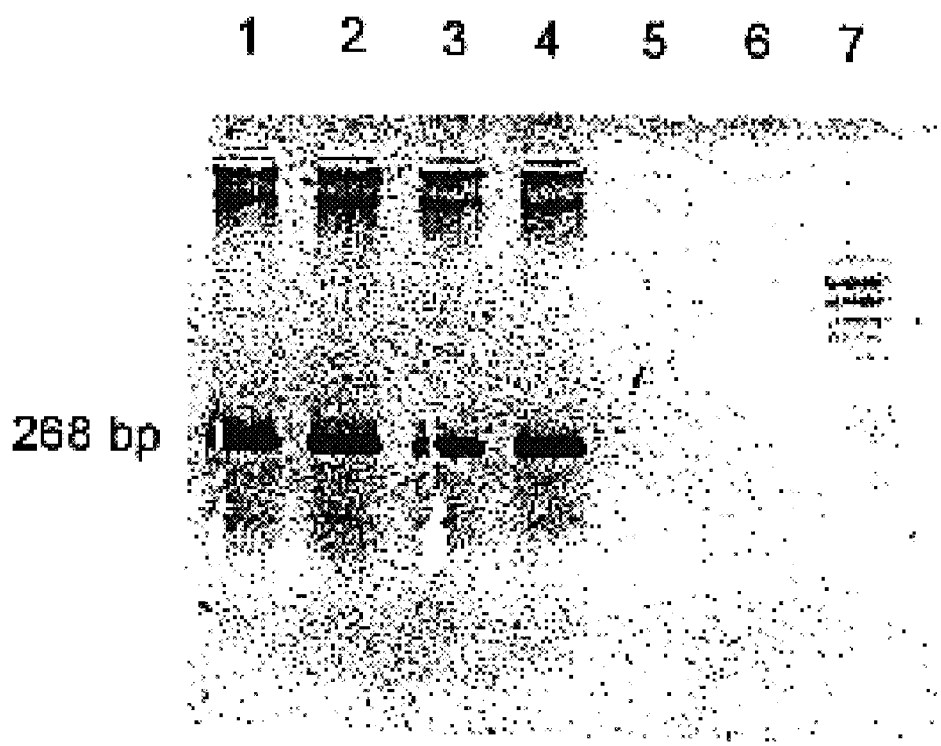
FIG. 1 shows the formation of a 268 base pair beta-globin fragment obtained by PCR from human DNA in the presence of the HPMC medium according to the invention and of a prior art tissue preservation medium.

In accordance with the present invention a medium is provided for embedding single cells or cell tissue to preserve, in a state suitable for DNA and/or RNA amplification, native DNA and/or RNA contained therein for an extended period of time at a temperature not exceeding 0° C., essentially consisting of an aqueous solution of one or several water-soluble cellulose derivatives and, optionally, of an osmotic pressure stabilizing agent.

Preferred water-soluble cellulose derivatives are selected from alkylated, hydroxy-alkylated, and alkylated/hydroxy-alkylated cellulose. Particularly preferred are hydroxyethyl cellulose, hydroxypropyl cellulose, methyl cellulose, ethyl cellulose, hydroxyethyl-methyl cellulose, hydroxyethyl-ethyl cellulose, hydroxypropyl-methyl cellulose. Most preferred is hydroxypropyl-methyl cellulose (HPMC).

Preferred DNA amplification methods comprise the polymerase chain reaction (PCR). Preferred RNA amplification methods comprise the reverse transcriptase polymerase chain reaction (RT-PCR).

The extended period of time for which native DNA and/or RNA can be preserved by the method of invention is two months or more at temperatures below 0° C., preferably at a temperature of −20° C. or less, most preferred at about −70° C. The term 'preserved' in particular designates the preserved capability of DNA and/or RNA amplification.

The osmotic pressure stabilizing agent may be any physiologically acceptable agent but includes preferably one or several of sodium chloride, potassium chloride, magnesium chloride.

Preferred concentrations of the soluble cellulose derivative range from about 0.1 to about 5% by weight. If a combination of soluble cellulose derivatives is used these figures indicate their total concentration.

The present invention also discloses a method of amplification of native DNA and/or native RNA, comprising:

procuring a sample containing native DNA and/or native RNA from a subject, an animal or from a single cell or a multitude of single cells;

providing the sample with a DNA/RNA preserving aqueous solution essentially consisting of one or several water-soluble cellulose derivatives and, optionally, an osmotic pressure stabilizing agent;

freezing the combination of sample and DNA/RNA preserving solution;

storing the frozen combination at a temperature of 0° C. or lower for an extended period of time;

bringing the frozen combination to a temperature above 0° C.;

removing all or part of the preserving solution by rinsing or washing;

optionally isolating the DNA and/or RNA from the sample;

amplifying the DNA and/or RNA.

In the method of the invention DNA is preferably amplified by polymerase chain reaction (PCR) and RNA is preferably amplified by reverse transcriptase polymerase chain reaction (RT-PCR).

Water-soluble cellulose derivatives useful in the method are selected from alkylated, hydroxy-alkylated, and alkylated/hydroxy-alkylated cellulose. In particular, they include hydroxyethyl cellulose, hydroxypropyl cellulose, methyl cellulose, ethyl cellulose, hydroxyethyl-methyl cellulose, hydroxyethyl-ethyl cellulose, hydroxypropyl-methyl cellulose. Most preferred is hydroxypropyl-methyl cellulose (HPMC).

According to a first preferred aspect of the invention is disclosed DNA obtained by amplification of DNA which had been kept in native form (in cells or tissues) embedded for an extended period of time at a temperature below 0° C. in an aqueous solution essentially consisting of a water soluble cellulose derivative and, optionally, an osmotic pressure stabilizing agent. Amplification is preferably by polymerase chain reaction (PCR).

According to a second preferred aspect of the invention is disclosed DNA obtained by amplification of RNA which had been kept embedded in native form in cells or tissues for an extended period of time at a temperature below 0° C. in an aqueous solution essentially consisting of a water soluble cellulose derivative and, optionally, an osmotic pressure stabilizing agent. Amplification is preferably by reverse transcriptase chain reaction (RT-PCR).

Further advantages and applications of the invention will become apparent by the study of the description of preferred embodiments of the invention and the claims.

METHODS

Cell Samples a) [for PCR] U2904 monoclonal B-lymphocytes of which the specific immunoglobulin gene serves as a clonal marker has been used as a positive PCR control for B-cell malignancies.

b) [for PCR] B-lymphocytes isolated from a patient with a suspected hemopathological disorder isolated with Lymphoprep® (Nycomed, Norway) and washed in PBS.

c) [for RT-PCR] t(9;22) positive cell line K562.

Cell Treatment and Storage.

Samples of about 50×10⁶ cells were pelleted.

Controls: Five samples were stored at −20° C., five at −70° C., being handled in the way which is standard for molecular pathological analysis, that is, without adding any reagents.

OCT-medium treated samples and HPMC-medium treated samples: Ten samples of each medium were covered with a layer of the respective medium. Of each medium, five samples were stored at −20° C. and five at −70° C.

Storage time was 2 months for all samples.

Preparation of RNA and DNA.

The pellets were thawed, washed twice with PBS by repeated re-suspension and centrifugation at about 20,000 g for 1 min to remove the embedding medium.

Cytoplasmatic RNA was prepared by adding to the t(9;22) positive K562 cell pellet an aqueous lysis buffer containg 0.14 M sodium chloride, 1.5 mM magnesium chloride am 10 mM Tris buffer of pH 8.6. In addition to 20 mM vanadyl ribonucleoside-complex and 1 mM dithiothreitol Nonidet P-40 was added to make a final concentration of 0.5% by weight. For lysis the cells were suspended in the lysis buffer and incubated on ice for 5 min. The suspension was centrifuged at 15,000×g for 1.5 min. The pellet of cell nuclei was used for the isolation of t(9;22) positive K562 genomic DNA. The supernatant was transferred to another tube and mixed with a protein digestion buffer containing 0.2 M Tris of pH 8.0, 0.3 M sodium chloride, 2% SDS and 80 ng/μl proteinase K. The solution was incubated at 56° C. for 30 min, thoroughly mixed with 500 μl phenol, and centrifuged for 5 min at 2,500×g. The upper phase was transferred to a new tube, mixed with 500 μl of cold isopropanol to precipitate RNA, centrifuged for 30 min at 15,000×g at a temperature of 4° C.; the RNA pellet thereby formed was dissolved in a suitable volume of aqueous DEPC. The DNA concentration was calculated to 300 ng/ml based on the fact that each cell contains 6 pg DNA, 5×10⁶ cells were lysed in 1,015 μl solution.

Genomic DNA from U2904 B-lymphocytes or the lymphocytes from the patient was prepared by adding 20 μl 1×PCR buffer per 10⁶ cells and proteinase K to a final concentration of 300 μg/ml. The cells were stored at 56° C. for 4 hrs, then heated to 95° C. for 4 min to inactivate proteinase K. After pelleting the cell debris 1 μl of the supernatant was used per PCR-reaction of 15 μl total volume. When using this method it was not possible to determine DNA concentration spectroscopically. The DNA concentration was calculated to 300 ng/μl based on the fact that each cell contains 6 pg DNA, 50×10⁶ cells were lysed in 1,015 μl solution PCR and RT-PCR.

Three PCR assays and one RT-PCR assay were used for determining the degree of degradation of native DNA by storage in various media. Two PCR assays with primer pairs generating fragments of 268 bp and 536 bp, respectively, were set up for detecting beta-globin which serves as a laboratory quality control for genomic DNA; the methods were optimized in regard of magnesium chloride concentration (1.5 mM). The third PCR assay concerned the detection of immunoglobulin genes using consensus primers used in clinical routine for detecting B-cell malignancies of various kind (M Deane and J D Norton, Immunoglobulin Gene "Fingerprinting", an Approach to Analysis of B-lymphoid Clonality in Lymphoproliferative Disorders. *British J. Haematol.* 1991, 77:274–281). The amplicons formed thereby vary from 280–350 bp. Genomic DNA from U2904 was used as template.

The RT-PCR assay using mRNA coding for beta-actin as target and specific primers generating a fragment with 392 bp was performed for analyzing isolated RNA.

The PCR and RT-PCR assays were performed in thermal cyclers (GeneAmp PCR System model 9600 and 9700, Perkin-Elmer Co.; the models were considered to provide equivalent results).

PCR and RT-PCR immunoglobulin gene analysis in D-cells: the reagents were purchased from Perkin-Elmer Co. USA. B-cell analysis: 5'-end primer VH3 (sequence: GGT CCC TGA GAC TCT CCT GTG CA (SEQ ID NO. 1)); 3'-end primer VLJH (sequence: ACC TGA GGA GAC GGT GAC CAG GGT (SEQ ID NO. 2)). The PCR reaction was performed in PCR-buffer II containing 50 mM KCl; 10 mM Tris HCl, pH 8.3; 0.5 µM primer; 3 mM magnesium chloride; 0.2 mM nucleotide (per nucleotide, using dUTP instead of dTTP); 0.025 U/µl AmpliTaq polymerase. To achieve a hot start the TaqStart antibody (Clontech Laboratories, Palo Alto, Calif.) had been added to the polymerase. Cycling conditions: 40 cycles of 95° C., 30 sec; 69° C., 30 sec; 72° C., 30 sec. Beta-globin analysis: 5'-end primer GH 20 (sequence: GAA GAG CCA AGG ACA GGT AC (SEQ ID NO. 3)); 3'-end primer PC 04 (sequence: CAA CTT CAT CCA CGT TCA CC (SEQ ID NO. 4)). The primer pair created an amplicon of 268 bp length. For obtaining an amplicon of 536 bp the 5'-end primer KM 29 was used (sequence: GGT TGG CCA ATC TAC TCC CAG G (SEQ ID NO. 5)) and the 3'-end primer RS 42 (sequence: GCT CAC TCA GTG TGG CAA AG (SEQ ID NO. 6)). The PCR reaction was performed under the same conditions as for the immunoglobulin gene, except that the concentration of magnesium chloride was 1.5 mM. The cycling conditions were also similar but for the annealing temperature which was 55° C.

For the beta-actin analysis two primers of the sequence TGG GTC ATC TTC TCG CGG TT (SEQ ID NO. 7) and GTG GGG CGC CCC AGG CAC CA (SEQ ID NO. 8), respectively, were used, producing an amplicon with a length of 392 bp. The RT-PCR reaction was performed with rtTH-enzyme (manufactured by Perkin-Elmer Corp.) as both reverse transcriptase and polymerase according to manufacturer's instructions. Manganese acetate concentration was 2.5 mM. Cycling conditions: 1 cycle of 60° C., 30 min and 94° C., 2 min; followed by 40 cycles of 94° C., 30 sec and 60° C., 1 min. Extension was performed at 72° C. for 2 min.

Electrophoresis of Amplicons and Genomic DNA.

To determine possible DNA degradation, electrophoresis in 2% agarose gel was performed with 10 µg of genomic DNA. The same gel medium was used for amplicon detection. Hae III cleaved Phix DNA (Promega, Madison, Wis.) was used as a DNA size marker. The loading buffer consisted of glycerol and bromophenolblue.

Determination of pH of Cell and Tissue Preservation Media.

Estimated by use of pH indicator sticks (Merck, Darmstadt); ranges pH 5–10 and 7.5–14.

Controls.

In the various experiments "control(s)" designates sample (s) of the respective cell type that had not been provided with cell preservation medium but had been treated otherwise in the same way as the samples provided with cell preservation medium.

Observations During the Preparation of RNA in the Presence of Cell Preservation Media.

When preparing RNA and DNA it was observed that the cell pellets frozen and stored with OCT medium at -70° C. were easily re-suspended in PBS. However, spinning of the re-suspended cells resulted in lysis; instead of a new pellet a viscous mass was formed which was impossible to separate from the supernatant. Isolation of RNA from the samples proved difficult or, in some instances, impossible.

Pellets frozen and stored with HPMC medium formed an agglutinized mass which was not easily re-suspended. When used for RNA preparation the HPMC medium treated agglutinized cells however behaved like untreated cells providing RNA in good yield. The preparation of RNA from untreated cells stored at -20° C. (FIG. 8) differed from that obtained from untreated cells stored at -70° C. in that it was not soluble in aqueous DEPC.

EXAMPLE 1

Effect of Added Cell Preservation Media to PCR.

Figure 2:
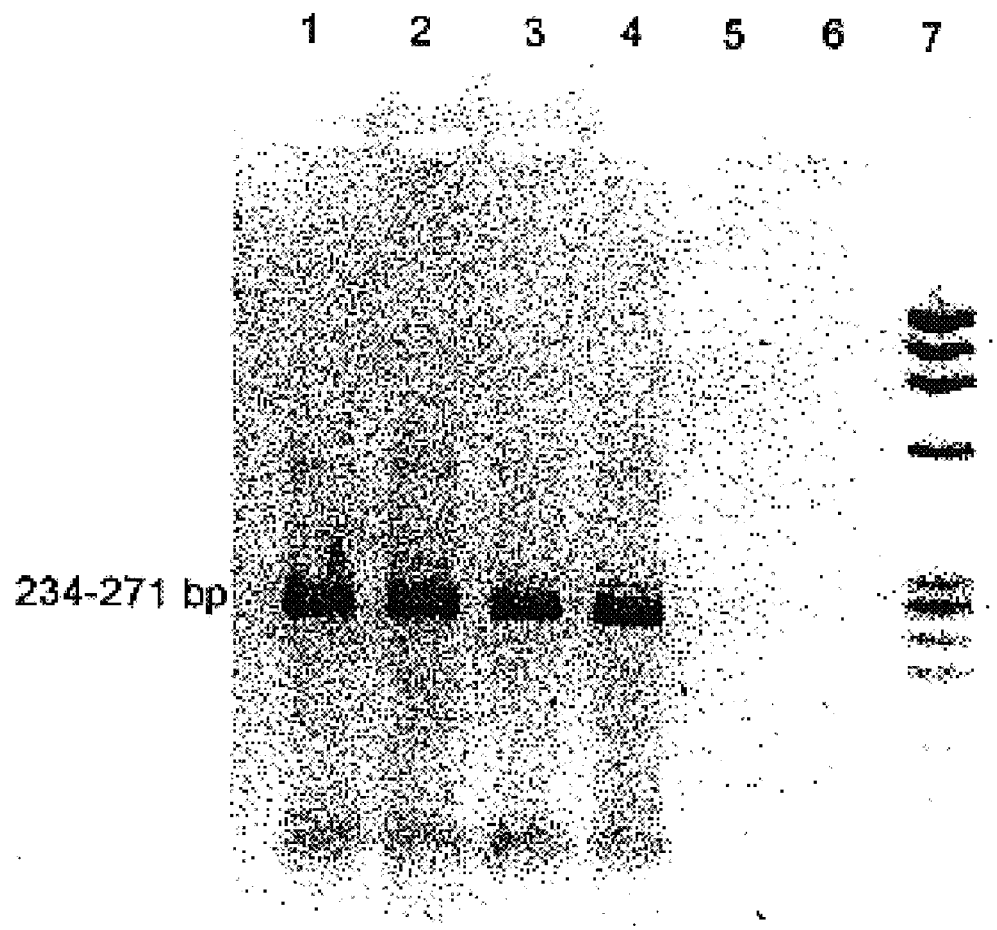
FIG. 2 shows the formation of a 392 bp beta-actin fragment obtained by RT-PCR of human DNA in the presence of the HPMC medium according to the invention and of a prior art tissue preservation medium.

10% (v/v) OCT medium or HPMC medium was added (3 µl to a 30 µl PCR reaction) to DNA prepared from fresh U2904 cells. This is considerably more embedding medium than could normally be expected to be left in DNA prepared from a piece of frozen tissue by mistake, such as bad rinsing, on a piece of frozen tissue. PCR (FIG. 1): beta-globin 268 bp amplicon. Lane identification: 1,2, positive controls; 3,4, HPMC 10% (v/v); 5,6 OCT 10% (v/v); 7, marker. RT-PCR (FIG. 2): beta-actin 392 bp amplicon. Lane identification: 1,2 positive controls; 3,4 HPMC 10% (v/v); 5,6 OCT 10% (v/v); 7, marker. As evident from FIGS. 1 and 2, PCR and RT-PCR assays are not affected by the presence of substantial amounts of HPMC medium according to the invention; corresponding amounts of the prior art cell preservation medium OCT are destructive to the same assays.

EXAMPLE 2

Effect of Adding Varying Amounts of Cell Preservation Media to PCR.

Figure 3:
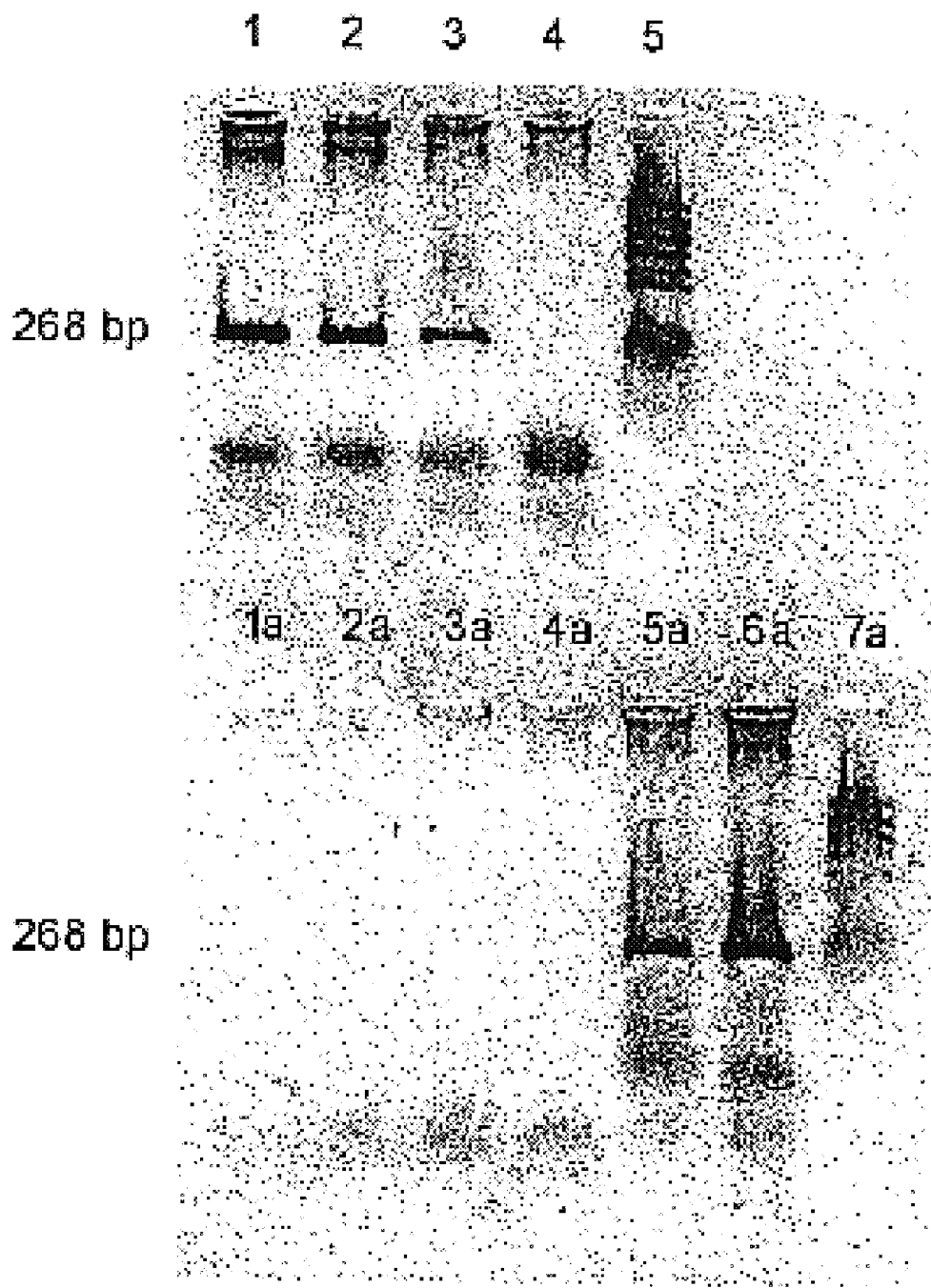
FIG. 3 shows the formation of the 268 bp beta-globin fragment of FIG. 1 obtained by PCR from the celline U2904 in the presence of the HPMC medium according to the invention and of a prior art tissue preservation medium.

Conditions as in Example 1. FIG. 3: beta-globin 268 bp amplicon. Lane identification: 1, HPMC 10% (v/v); 2, HPMC 20% (v/v); 3, HPMC 30% (v/v); 4, HPMC 40% (v/v); 5, marker; 1a, OCT 10% (v/v); 2a, OCT 5% (v/v); 3a, OCT 2.5% (v/v); 4a, OCT 1.25% (v/v); 5a, OCT 1% (v/v); 6a (0.5); 7a, marker. As shown in FIG. 3 the PCR is not affected by the HPMC medium according to the invention in a concentration of 30% (v/v) while the prior art OCT medium is destructive at concentrations (v/v) above about 1%.

EXAMPLE 3

Preservation of Genomic DNA in Cells Stored in the Presence of Cell Preservation Media.

Figure 4:
FIG. 4 shows the formation of the 536 bp beta-globin fragment by PCR from genomic DNA obtained from the B-lymphocyte U2904 cells stored at −70° C. in the presence of the HPMC medium according to the invention and of a prior art tissue preservation medium.
Figure 5:
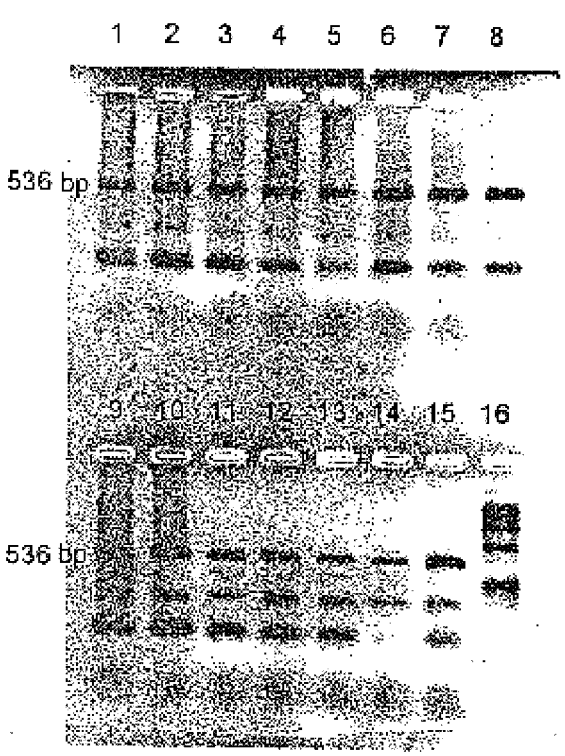
FIG. 5 shows the formation of the 536 bp beta-globin fragment by PCR from genomic DNA obtained from B-lymphocyte U2904 cells stored at −20° C. in the presence of the HPMC medium according to the invention and of a prior art tissue preservation medium.
Figure 6:
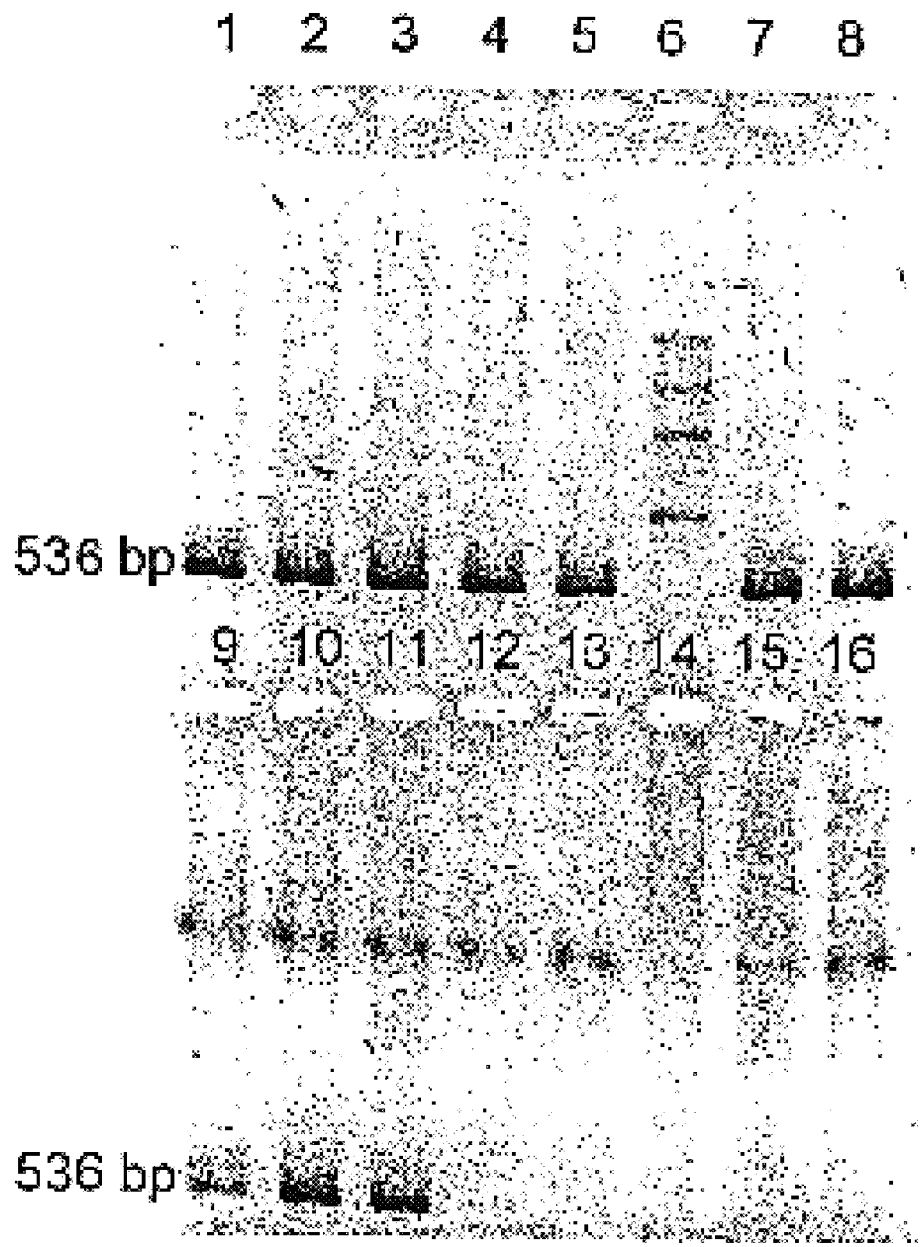
FIG. 6 is the experiment of FIG. 4, duplicated.

Genomic DNA fragment size analysis on agarose (FIG. 4) demonstrated that degradation of DNA in OCT-treated U2904 cells stored at -20° C. (gel 2 lanes 11–15) was virtually complete while a PCR assay (showed that, in some samples, there was enough DNA left as template for amplification (FIG. 5, gel 2 lanes 11–15). Similar results were obtained at a storage temperature of -70° C. (FIGS. 4 and 6). In contrast, DNA from cells treated with HPMC medium according to the invention produced large amounts of amplicons in all samples at both storage temperatures. The yield of amplicons was significantly lower in PCR with long fragments (536 bp) than with short fragments (268 bp; Example 2). FIG. 6; lane identification: 1–5, controls; 6, marker; 7–11, HPMC (lagringstid); 12–16, OCT (temperatur)

EXAMPLE 4

Preservation of Cytoplasmatic RNA Cells in Stored in Cell Preservation Media.

Figure 7:
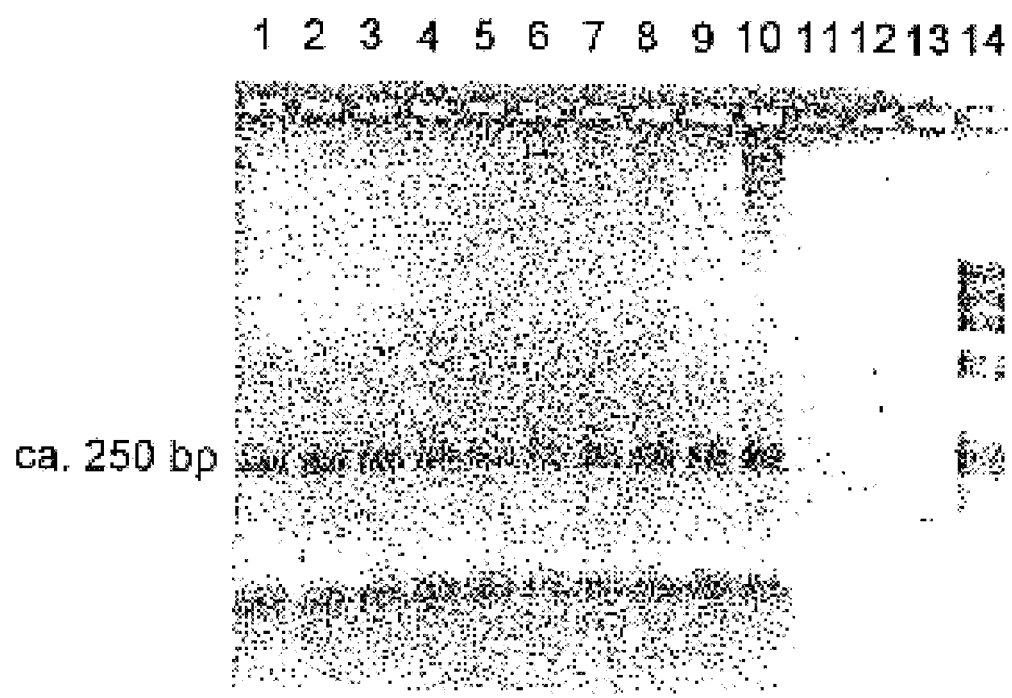
FIG. 7 shows the formation of 392 bp beta-actin fragments by RT-PCR from cytoplasmatic RNA obtained from t(99;22) positive K562 cells stored at −70° C. in the presence of the HPMC medium according to the invention and of a prior art tissue preservation medium.
Figure 8:
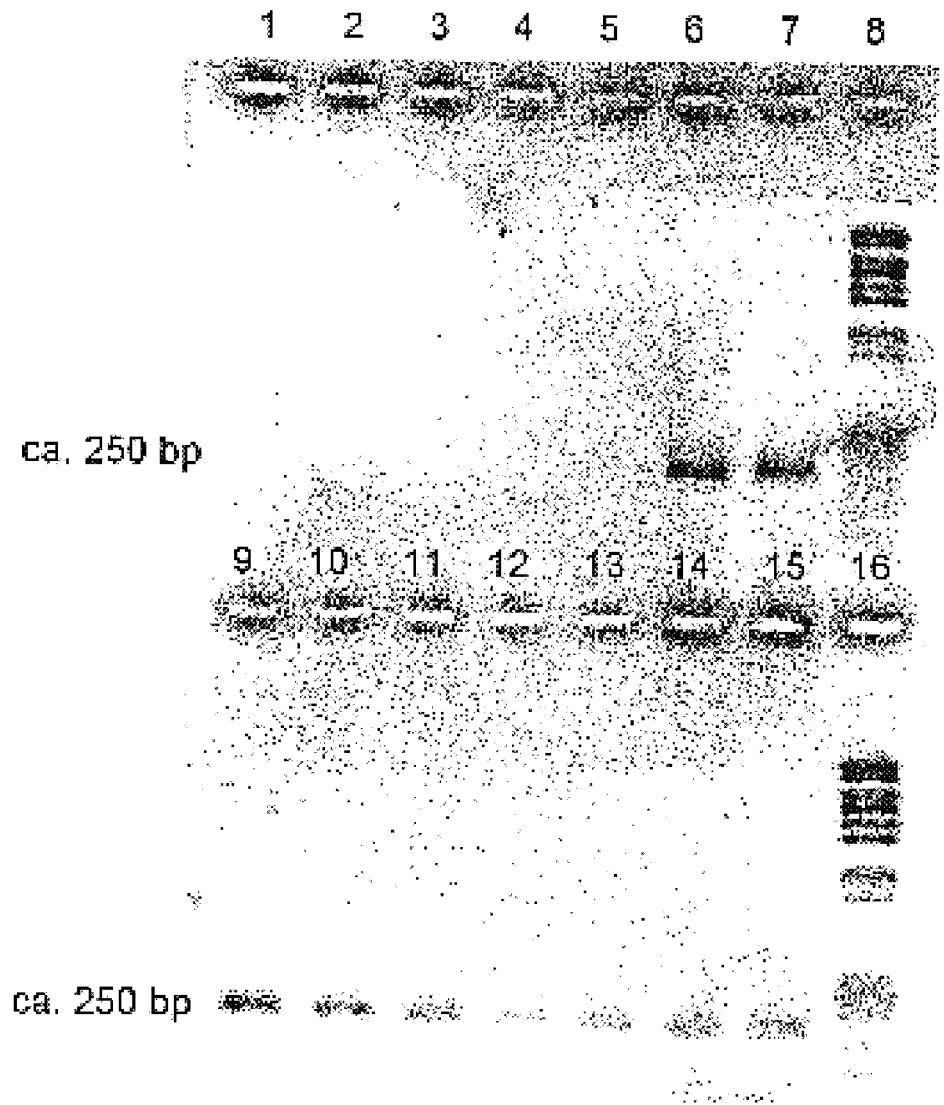
FIG. 8 shows the formation of 392 bp beta-actin fragments by RT-PCR from cytoplasmatic RNA obtained from t(99;22) positive K562 cells stored at −70° C. in the presence of the HPMC medium according to the invention and of a prior art tissue preservation medium.

RT-PCR with RNA isolated from stored U2904 cells: beta-actin, appr. 392 bp PCR fragment. FIG. 7; storage temperature −70° C.; lane identification: 1–5, controls; 6–10, HPMC; 14, marker. FIG. 8; storage temperature −20° C.; lane identification: 1–5, OCT controls; 6,7,9–11 HPMC; 8, marker; 12–15, OCT 16, marker. From FIGS. 7 and 8 it is evident that the preservation of cytoplasmatic RNA with OCT medium is sluggish, whereas it is good with the HPMC medium according to the invention. While preservation at −70° C. is good even in the absence of a preservation medium, no preservation at a storage temperature of −20° C. was observed in absence of medium.

Comments to the Examples in Regard of the OCT Medium.

One would expect that DNA in cells stored at −20° C. would be more affected by OCT medium than cells stored at −70° C. This is however not true. While two of five samples stored at −70° C. could not be amplified at all, all five samples stored at −20° contained amplifiable DNA but amplicons of much poorer quality than untreated cells or cells treated with the HPMC medium according to the invention, as demonstrated by the number of amplicons produced (cf. FIG. 5).

What is claimed is:

1. A method of amplification of native DNA and/or native RNA, comprising:

procuring a sample containing native DNA and/or native RNA from a subject, an animal or from a single cell or a multitude of single cells;

combining the sample with a DNA/RNA preserving aqueous solution consisting of at least one water-soluble cellulose derivative water;

freezing the combination of sample and DNA/RNA preserving solution;

storing the frozen combination at a temperature of 0° C. or lower for a period of time of at least two months;

bringing the frozen combination to a temperature above 0° C.;

removing all or part of the preserving solution by rinsing or washing;

optionally isolating the DNA and/or RNA from the sample; and amplifying the DNA and/or RNA.

2. The method of claim 1, wherein DNA is amplified by polymerase chain reaction (PCR).

3. The method of claim 1, wherein RNA is amplified by reverse transcriptase polymerase chain reaction (RT-PCR).

4. The method of claim 1, wherein said water-soluble cellulose derivative is selected from the group consisting of alkylated, hydroxy-alkylated, and alkylated/hydroxy-alkylated cellulose.

5. The method of claim 4, wherein said water-soluble cellulose derivative is selected from the group consisting of hydroxyethyl cellulose, hydroxypropyl cellulose, methyl cellulose, ethyl cellulose, hydroxyethyl-methyl cellulose, hydroxyethyl-ethyl cellulose, and hydroxypropyl-methyl cellulose.

6. The method of claim 5, wherein said soluble cellulose derivative is hydroxypropyl-methyl cellulose.

7. A method of amplification of native DNA and/or native RNA, comprising:

procuring a sample containing native DNA and/or native RNA from a subject, an animal or from a single cell or a multitude of single cells;

combining the sample with a DNA/RNA preserving aqueous solution consisting of at least one water-soluble cellulose derivative, water and, optionally, an agent that stabilizes osmotic pressure;

freezing the combination of sample and DNA/RNA preserving solution;

storing the frozen combination at a temperature of 0° C. or lower for a period of time of at least two months;

bringing the frozen combination to a temperature above 0° C.;

removing all or part of the preserving solution by rinsing or washing;

optionally isolating the DNA and/or RNA from the sample; and amplifying the DNA and/or RNA.

8. The method of claim 7, wherein DNA is amplified by polymerase chain reaction (PCR).

9. The method of claim 7, wherein RNA is amplified by reverse transcriptase polymerase chain reaction (RT-PCR).

10. The method of claim 7, wherein said water-soluble cellulose derivative is selected from the group consisting of alkylated, hydroxy-alkylated, and alkylated/hydroxy-alkylated cellulose.

11. The method of claim 10, wherein said water-soluble cellulose derivative is selected from the group consisting of hydroxyethyl cellulose, hydroxypropyl cellulose, methyl cellulose, ethyl cellulose, hydroxyethyl-methyl cellulose, hydroxyethyl-ethyl cellulose, and hydroxypropyl-methyl cellulose.

12. The method of claim 11, wherein said soluble cellulose derivative is hydroxypropyl-methyl cellulose.

* * * * *

SEQUENCE LISTING

```
<160> NUMBER OF SEQ ID NOS: 8

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      Construct

<400> SEQUENCE: 1
ggtccctgag actctcctgt gca                                            23

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      Construct

<400> SEQUENCE: 2
acctgaggag acggtgacca gggt                                           24

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      Construct

<400> SEQUENCE: 3
gaagagccaa ggacaggtac                                                20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      Construct

<400> SEQUENCE: 4
caacttcatc cacgttcacc                                                20

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      Construct
```

-continued

```
<400> SEQUENCE: 5
ggttggccaa tctactccca gg                                              22

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      Construct

<400> SEQUENCE: 6
gctcactcag tgtggcaaag                                                 20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      Construct

<400> SEQUENCE: 7
tgggtcatct tctcgcggtt                                                 20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      Construct

<400> SEQUENCE: 8
gtggggcgcc ccaggcacca                                                 20
```